(12) United States Patent
Reed et al.

(10) Patent No.: US 10,197,500 B2
(45) Date of Patent: Feb. 5, 2019

(54) SYSTEMS AND METHODS FOR PREDICTING AND CONTROLLING THE PROPERTIES OF A CHEMICAL SPECIES DURING A TIME-DEPENDENT PROCESS

(71) Applicants: ADVANCED POLYMER MONITORING TECHNOLOGIES, INC., New Orleans, LA (US); THE ADMINISTRATORS OF THE TULANE EDUCATIONAL FUND, New Orleans, LA (US)

(72) Inventors: Wayne Frederick Reed, New Orleans, LA (US); Michael Felix Drenski, New Orleans, LA (US)

(73) Assignees: ADVANCED POLYMER MONITORING TECHNOLOGIES, INC., New Orleans, LA (US); THE ADMINISTRATORS OF THE TULANE EDUCATIONAL FUND, New Orleans, LA (US)

(*) Notice: Subject to any disclaimer, the term of this patent is extended or adjusted under 35 U.S.C. 154(b) by 0 days.

(21) Appl. No.: 15/544,176

(22) PCT Filed: Jan. 19, 2016

(86) PCT No.: PCT/US2016/013915
§ 371 (c)(1),
(2) Date: Jul. 17, 2017

(87) PCT Pub. No.: WO2016/118507
PCT Pub. Date: Jul. 28, 2016

(65) Prior Publication Data
US 2018/0011024 A1    Jan. 11, 2018

Related U.S. Application Data

(60) Provisional application No. 62/106,555, filed on Jan. 22, 2015.

(51) Int. Cl.
    *G01N 21/75*      (2006.01)
    *G01N 21/27*      (2006.01)
    (Continued)

(52) U.S. Cl.
    CPC .............. *G01N 21/75* (2013.01); *B01J 8/001* (2013.01); *B01J 8/006* (2013.01); *B01J 8/222* (2013.01);
    (Continued)

(58) Field of Classification Search
CPC ........ G01N 21/75; G01N 21/84; G01N 11/02; G01N 35/00; B01J 8/001; B01J 19/0006
(Continued)

(56) References Cited

U.S. PATENT DOCUMENTS

| | | |
|---|---|---|
| 7,122,379 B2 | 10/2006 | Wolf et al. |
| 8,322,199 B2 | 12/2012 | Reed |
| 2012/0085151 A1 | 4/2012 | Konrad et al. |

FOREIGN PATENT DOCUMENTS

| | | |
|---|---|---|
| JP | 2002-201228 A | 7/2002 |
| JP | 2011-525967 A | 9/2011 |
| WO | 03/006955 A1 | 1/2003 |

OTHER PUBLICATIONS

PCT Search Report and Written Opinion dated Mar. 31, 2016 in corresponding PCT Application No. PCT/US2016/013915, filed Jan. 19, 2016 to Advanced Polymer Monitoring Technologies, Inc. et al., 10 pages.

(Continued)

*Primary Examiner* — Fred M Teskin
(74) *Attorney, Agent, or Firm* — Polsinelli PC

(57) ABSTRACT

Devices and methods for controlling the properties of chemical species during time-dependent processes. A device includes a reactor for containing one or more chemical species of a time-dependent process, an extraction pump for (Continued)

automatically and continuously extracting an amount of the one or more chemical species from the reactor, one or more detectors for measuring property changes of the one or more extracted chemical species and generating a continuous stream of data related to the one or more property changes to the one or more chemical species during a time interval, and a process controller configured to fit the continuous stream of data to a mathematical function to predict one or more properties of the one or more chemical species at a future time point and make one or more process decisions based on the prediction of one or more properties at the future time point.

20 Claims, 8 Drawing Sheets

(51) Int. Cl.
    *G01N 21/84*     (2006.01)
    *G01N 35/00*     (2006.01)
    *B01J 8/00*     (2006.01)
    *B01J 19/00*     (2006.01)
    *B01J 19/18*     (2006.01)
    *B01J 8/22*     (2006.01)
    *G01N 21/19*     (2006.01)
    *G01N 21/21*     (2006.01)
    *G01N 21/23*     (2006.01)
    *G01N 21/33*     (2006.01)
    *G01N 21/35*     (2014.01)
    *G01N 21/47*     (2006.01)
    *G01N 21/64*     (2006.01)
    *G01N 21/65*     (2006.01)
    *G01N 11/08*     (2006.01)

(52) U.S. Cl.
    CPC ........... B01J 8/228 (2013.01); B01J 19/0006 (2013.01); B01J 19/18 (2013.01); B01J 19/1881 (2013.01); G01N 21/272 (2013.01); G01N 21/84 (2013.01); *B01J 2208/00061* (2013.01); *B01J 2208/00212* (2013.01); *B01J 2208/00362* (2013.01); *B01J 2208/00539* (2013.01); *B01J 2208/00548* (2013.01); *B01J 2208/00575* (2013.01); *B01J 2208/00628* (2013.01); *B01J 2208/00637* (2013.01); *B01J 2208/00725* (2013.01); *B01J 2208/00973* (2013.01); *B01J 2219/002* (2013.01); *B01J 2219/0004* (2013.01); *B01J 2219/0024* (2013.01); *B01J 2219/00063* (2013.01); *B01J 2219/00069* (2013.01); *B01J 2219/00072* (2013.01); *B01J 2219/00094* (2013.01); *B01J 2219/00123* (2013.01); *B01J 2219/00164* (2013.01); *B01J 2219/00168* (2013.01); *B01J 2219/00186* (2013.01); *B01J 2219/00216* (2013.01); *B01J 2219/00218* (2013.01); *B01J 2219/00225* (2013.01); *B01J 2219/00231* (2013.01); *B01J 2219/00236* (2013.01); *B01J 2219/00238* (2013.01); *B01J 2219/00243* (2013.01); *B01J 2219/00272* (2013.01); *G01N 11/08* (2013.01); *G01N 21/19* (2013.01); *G01N 21/21* (2013.01); *G01N 21/23* (2013.01); *G01N 21/33* (2013.01); *G01N 21/35* (2013.01); *G01N 21/47* (2013.01); *G01N 21/64* (2013.01); *G01N 21/65* (2013.01); *G01N 2021/8416* (2013.01); *G01N 2201/12* (2013.01)

(58) Field of Classification Search
    USPC ............................... 422/62; 526/59; 700/269
    See application file for complete search history.

(56)              References Cited

OTHER PUBLICATIONS

Ehabe et al., "Modelling of Mooney Viscosity Relaxation in Natural Rubber," Polymer Testing, vol. 24, 2005, pp. 620-627.

SYSTEMS AND METHODS FOR PREDICTING AND CONTROLLING THE PROPERTIES OF A CHEMICAL SPECIES DURING A TIME-DEPENDENT PROCESS

CROSS REFERENCE TO RELATED APPLICATIONS

This application claims priority from U.S. provisional application no. 62/106,555, entitled "SYSTEMS AND METHODS FOR PREDICTING AND CONTROLLING THE PROPERTIES OF A CHEMICAL SPECIES DURING A TIME-DEPENDENT PROCESS," filed on Jan. 22, 2015, which is incorporated by reference in its entirety, for all purposes, herein.

FIELD OF TECHNOLOGY

This specification is directed to systems and methods for controlling the properties of a chemical species during a time-dependent process.

BACKGROUND

Using online monitoring data for predicting when a chemical species involved in a time-dependent process arrives at a certain property allows for more precise control and efficiency of such processes. Some examples of time-dependent processes are predicting when filling a gas tank will reach a certain level or will run dry under given consumption conditions, when individual reactants being mixed will form a desired composition, when a drying substance or material will reach a certain humidity level, when an active battery will be fully drained, when a chemical reaction will reach a desired state, and so on.

Monitoring the properties of chemical species during time-dependent processes is of growing importance for process control in the polymer, natural product, biotechnology, and other sectors. Improved systems and methods for controlling the properties of a chemical species during time-dependent polymerization processes are disclosed herein.

SUMMARY

This specification is directed to improved systems and methods for controlling the properties of chemical species during time-dependent polymerization processes.

The foregoing and other objects, features and advantages of the present disclosure will become more readily apparent from the following detailed description of exemplary embodiments as disclosed in this specification.

Figure 1:
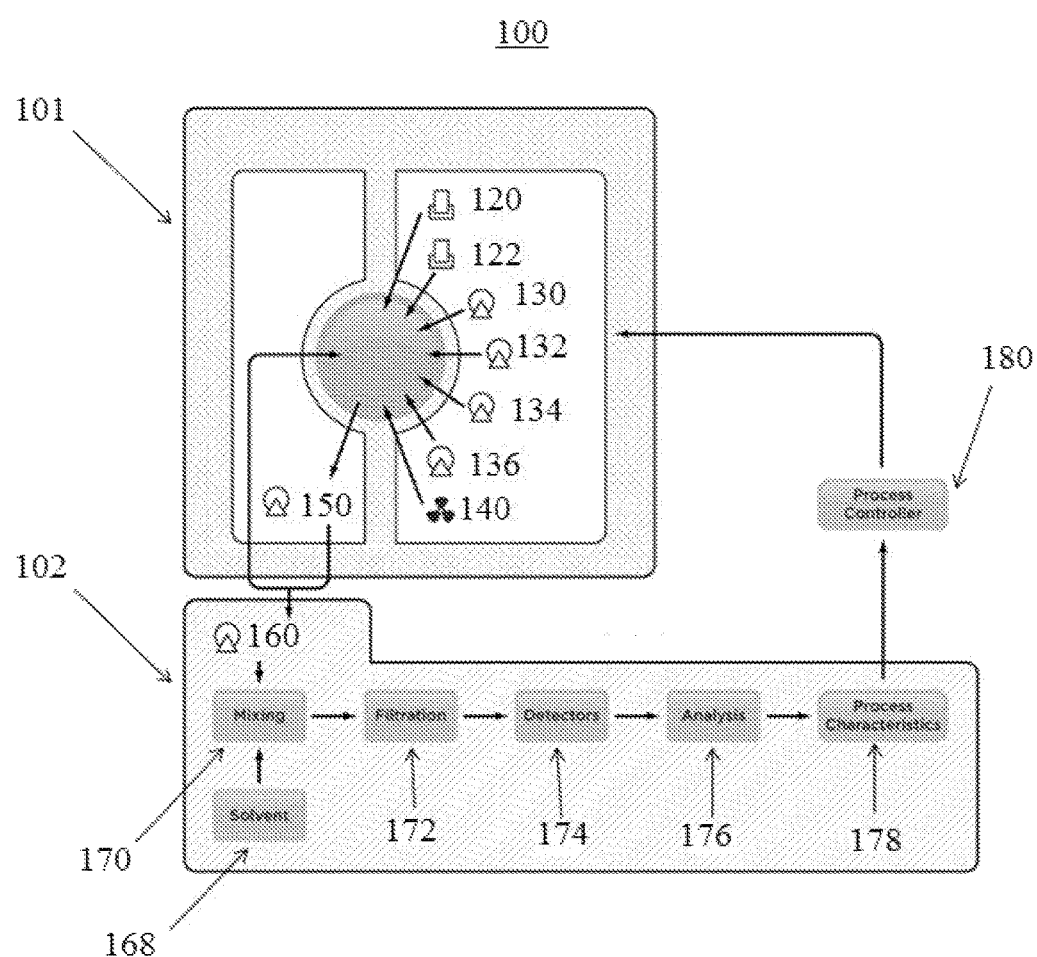
FIG. 1 is a diagram of an exemplary polymerization reaction process control and monitoring system for controlling the properties of chemical species during time-dependent polymerization processes in accordance with an exemplary embodiment of the present disclosure.

It should be understood that the various aspects are not limited to the arrangements and instrumentality shown in the drawings.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

Several definitions that apply throughout this disclosure will now be presented. The term "coupled" is defined as connected, whether directly or indirectly through intervening components, and is not necessarily limited to physical connections. The term "communicatively coupled" is defined as connected, either directly or indirectly through intervening components, and the connections are not necessarily limited to physical connections, but are connections that accommodate the transfer of data between the so-described components. The connections can be such that the objects are permanently connected or releasably connected. The term "outside" refers to a region that is beyond the outermost confines of a physical object. The term "axially" means substantially along a direction of the axis of the object. If not specified, the term axially is such that it refers to the longer axis of the object. The terms "comprising," "including" and "having" are used interchangeably in this disclosure. The terms "comprising," "including" and "having" mean to include, but are not necessarily limited to, the things so described. A "processor" or "process controller" as used herein is an electronic circuit that can make determinations based upon inputs and can actuate devices in response to the determinations made. Devices that can be actuated include, but are not limited to, pumps, gas flow controllers, temperature controllers, and stirring controllers.

A processor or process controller can include a microprocessor, a microcontroller, and/or a central processing unit, among others. While a single processor can be used, the present disclosure can be implemented using a plurality of processors.

Monitoring the properties of chemical species during time-dependent processes is of growing importance for process control in polymer, natural product, biotechnology, and other sectors. Some non-limiting examples addressed by the technology disclosed herein are discussed below.

National regulatory agencies put strict limits on the amounts of residual monomers or organic solvents that can be used in products. These include, but are not limited to bisphenol-A, acrylamide ("Am"), many acrylates, methacrylates, ethacrylates, hexane, chlorinated solvents such as chloroform or dichloromethane, various forms of acrylic acids, vinyl chloride, and other similar chemical species. Determining residual monomer content during polymer reactions is particularly challenging and is currently carried out manually in many polymer manufacturing sectors. In such cases, a plant operator or technician typically withdraws sample from the reactor, and submits it to an analytical laboratory for analysis of residual monomer concentration and other reaction characteristics (for example, the molecular weight distribution of the polymer product). The residual can then be analyzed by a variety of means which include but are not limited to High Performance Liquid Chromatography ("HPLC"), Gas Chromatography ("GC"), and combined methods such as GC-mass spectrometry (GC-MS), Matrix-Assisted Laser Desorption/Ionization Time-of-Flight Mass Spectrometry ("MALDI-TOF"), Gel Permeation Chromatography (GPC), and so on.

Such determinations are labor intensive and add significant delay between measurement of the withdrawn material and the actual current status of the reaction. These measurements are often used to determine product completion and sometimes also for process control purposes. Typically, delays of one hour or more are common. Unlike the above referenced means of analysis, the presently disclosed technology continuously provides predictions of when acceptable residual levels occur.

Another example to which the presently disclosed technology can be applied is the prediction of when a grade changeover will reach a satisfactory level during grade changeover in a continuous reactor. This can occur whenever two or more materials are mixed and a specific composition is desired, or obtaining a specific material with a minimum amount of the others. An example of this is grade changeover in a continuous polymer reaction process. Generally, manufacturers produce a certain grade at a steady state and then wish to change to another grade. In this instance, one must wait for the changeover of products to reach an acceptable level before starting to accumulate product off the new steady state. If the second product is accumulated too early, the second product risks being adulterated with the first product, whereas any delay beyond an acceptable level of changeover represents wasted product and time. Another example would be a blending application where two or more different products are blended to achieve a desired property (for example, Product A with high viscosity properties and Product B with low viscosity properties blended to make Product C with properties somewhere near an average of the two input products). Blending different products is very common in the industry. The presently disclosed technology allows for continuous predictions of when an acceptable changeover or appropriate blend level will occur during the polymerization reaction.

Another example is post-polymerization functionalization of polymers, in which an initially produced polymer serves as a backbone or scaffold on which modifications are made. These include, but are not limited to, grafting reactions where short, medium or long branches are covalently coupled with the initial polymer, sulfonation, amination, acid and base hydrolysis, carboxylation, PEGylation, and many more such processes. Hybrid polymers are also frequently produced, in which the starting material is a natural product (biopolymer), such as, for example, a polysaccharide or protein, and synthetic chemical groups are attached to or grown onto the biopolymers. Hybrid particles with grafts are often classified as to those for which ready-made grafts are attached to the backbone polymer and those for which the graft is grown from the polymer. The same applies for hybrid particles, such as, for example, silica, carbon nanotubes, titanium dioxide, and other nano- and microparticles to which polymer grafts can be attached and from which grafts can be grown.

The presently disclosed technology provides many benefits to the chemical industry. These benefits include, for example, improvements in production yield, product quality, production cost, worker safety, and product safety.

The presently disclosed technology requires a continuous stream of data that is related to the concentration or other property, such as molecular weight, of chemical species in a solution. Examples of data that can contain such information include Ultraviolet/Visible absorption (UV), refractivity (RI), conductivity, laser light scattering intensity, dynamic light scattering, Mie scattering, evaporative light scattering, intrinsic viscosity, absorption in other electromagnetic spectral regions (for example, infra-red), fluorescence, polarimetry, linear dichroism, circular dichroism, linear birefringence, circular birefringence, Raman scattering, ultrasound, nuclear magnetic resonance (NMR), and so on.

An exemplary instrument that can furnish the types of continuous data required for the presently disclosed technology is an Automatic Continuous Online Monitoring of Polymerization reactions (ACOMP) instrument. See for example, F. H. Florenzano, R. Strelitzki, W. F. Reed, "Absolute, Online Monitoring of Polymerization Reactions", Macromolecules, 31, 7226-7238, 1998; and W. F. Reed, "Automatic Continuous Online Monitoring of Polymerization Reactions (ACOMP)", Encyclopedia of Analytical Chemistry, Elsevier, October 2013, DOI: 10.1002/9780470027318.a9288.

The term "continuous," as used herein, means that data points during a time-dependent process are collected at a frequency sufficient to allow for accurate measurements and predictions of one or more physical or chemical properties related to chemical species to be made with the precision required to bracket the particular properties into an acceptable range, according to requirements placed on a product due to quality issues, safety, regulatory concerns, and so on. Typically, a few hundred to several thousand data points are taken per detected signal during the reaction.

The term 'substantially continuous' can also be used and defined as follows: If a sufficient number of data points can be gathered over the period of the process that the maximum amount of change in a signal between any two points does not exceed some limit, then the measurement is substantially continuous. As a non-limiting example, it could be specified that between two successive data points there should not be more than a maximum change of 1% of, for example, the light scattering signal compared to its entire variation from $t=0$ until the end of measurement of the process. Thus, for example, for a process lasting 1,000 seconds, and for which a change of 1% of the entire light scattering change occurs on the scale of 5 seconds, then at least two hundred points spaced by five seconds would need to be gathered to make this measurement substantially continuous. For a process lasting 10 days, where a change of 1% of the entire light scattering occurs on the scale of 5 minutes, at least 2,880 points would need to be gathered over 10 days, each spaced 5 minutes apart. There is no requirement that sampling points be equally spaced in time, although this will often be the simplest method.

The term "chemical species," as used herein in a general sense, means reactants, chemical catalysts or initiators, enzymes, acids, or other reagents that aid a reaction, beneficial or toxic molecules produced in a bio-reaction, or beneficial or toxic molecules produced during the processing of natural products. The term "reactant," as used herein, means a substance that changes when it is combined with another substance in a chemical reaction, such as, for example, monomers and comonomers used in the formation of a copolymer and compounds for the functionalization of polymers, copolymers, block copolymers, and the like. The term "reagent," as used herein, means a compound or mixture added to a system to cause a chemical reaction, to cause a change in the rate of a chemical reaction, to provide a medium to support the chemical reaction, or test if a chemical reaction occurs. For example, reagents include, but are not limited to, solvents, gases, quenching agents, catalysts, detector standards or reference compounds, and so on. By the above definitions, both reactants and reagents constitute chemical species.

The term "monomer," as used herein, is a single molecule of a chemical species used as building block in the synthesis of polymers.

The term "reaction," as used herein, can refer to any number of time-dependent processes involving one or more chemical species, including monomers, polymers and/or colloids in solution. Reactions can involve the formation or breaking of covalent chemical bonds, making or breaking of physical bonds (for example, van der Waals or hydrogen bonding), changes in phases, changes in conformational states of macromolecules, oxidation, and so on. The time-dependent process may also take the form of a dilution, mixing of chemical species, blending of different product grades, constructing polymers through grafting or other multi-part addition processes, changeover of product grades during a polymerization reaction (that is, when a manufacturer produces "Product A" in a continuous reactor and then makes a production transition to "Product B" in the continuous reactor), and so on. Reactions can be performed in a homogeneous phase, a heterogeneous phase, or a bulk phase. Examples of polymers and copolymers of interest include, but are not limited to, those containing such monomers as styrene and similar monomers such as divinyl benzene and styrene sulfonate, any of the family of acrylamides and acrylamide derivatives, including anionic and cationic derivatives, vinyl pyrrolidone, any monomers in the families of acrylate, methacrylates, ethacrylates, vinyl chloride, olefins such as ethylene, propylene, and butadiene, sulfones, acrylonitrile, vinyl alcohol. The method can also be used for processes involving natural products such as proteins, polysaccharides, nucleic acids, and combinations of these, as well as hybrid materials involving grafts of biopolymers and synthetic polymers, such as, but not limited to, polyethylene glycol grafted to synthetic polymers, and amino acids or proteins grafted to synthetic polymers.

Another example of chemical reactions, as defined herein, is in the area of non-covalent polymers. These are polymers that form physical, often reversible, non-covalent associations from 'monomers' under specific conditions, such as temperature, concentration of the monomers, solvent pH, ionic strength, presence of molecules such as surfactants, specific ions, covalent polymers, and colloids. Hydrogen bonds, for example, are often used to create the physical, non-covalent linkages of non-covalent polymers. See, for example, A. J. Wilson, "Non-covalent polymer assembly using arrays of hydrogen bonds, Soft Matter, 3 (2007) 409-425. Physical linkage by hydrophobic self-assembly is also possible. See, for example, J. Baram et al., "Hydrophobic self-assembly affords robust noncovalent polymer isomers, Angewandte Chemie, Int'l. Edition, 53 (2014) 4123-4126.

The current technology can also be applied to reactions involving small molecules, rather than those involving polymers. Such reactions include the conversions of one organic species into others. Examples include, but are not limited to, Friedel-Crafts acylation, Diels-Alder cycloaddition reactions, Kiliani-Fischer synthesis of aldoses, alkane preparation by Wurtz reaction, Markovnikov and anti-Markovnikov preparation of alkenes, and the Huisgen azide-alkyne cycloaddition.

The usual approach to determining chemical species concentrations with the aforementioned types of detectors is to establish a calibration between the detector response and the concentration of the chemical species to be measured. Invariably, a 'baseline' or 'blank' measurement is required to establish such a concentration. This baseline or blank measurement is normally made against a substance, such as a liquid, in which the reaction will occur, without the presence of any of the chemical species to be monitored. Measurement of known concentrations of the chemical species in the solution, or use of known calibration factors (for example, UV extinction coefficients, refractive index increments, specific conductivity, and fluorescence) then allow the concentrations of the chemical species to be computed as the reaction is carried out. This direct 'static' method works properly as long as no other species add or subtract from these signals during the reaction. If other species contribute to the measured signals, then the concentration, determined under the assumption of only the one or more chosen chemical species contributing to the signals, will be erroneous. If independent measures of the other species that contribute to the signals can be made, then their effects can be subtracted out to recover the true concentrations of the species under study. One example of this can be seen when a charged molecule has the same UV absorbance as the chemical species to be monitored. An independent conductivity measurement might suffice to determine the concentration of the charged species so that its effect can be subtracted from the UV absorbance.

The currently presented technology is suited for, but not limited to, the situation where one or more chemical species interferes with the signals measured for monomer concentration determination. This interference can be due to constant concentrations of such chemical species or where such chemical species are changing in concentration during the reaction. For example, chemical species that can interfere with measurements include, but are not limited to, desired reaction end products and reaction side products.

Another instance where the presented technology can be used is during the modification of a polymer. For example, a polymer can be functionalized after it is produced by such means as hydrolysis, sulfonation, amination, carboxylation, quaternization, PEGylation, and many other processes. During such treatment, properties of the polymer can change, such as composition, net electrical charge, molecular weight distribution, intrinsic viscosity, solubility, tendency to aggregate or form supramolecular structures, and other properties. The end point of such a process may not be well known but the currently presented technology allows continuous or substantially continuous monitoring data to be used to form mathematical extrapolations as to intermediate and final points in the process. For example, electrically neutral polyacrylamide can be hydrolyzed by sodium hydroxide to form electrically charged carboxylates along the chain. This leads to a swelling of the polymer chains and a corresponding increase in polymer intrinsic viscosity. The intrinsic viscosity depends on both the degree of carboxylation and the ionic strength of the supporting medium; the higher the ionic strength the lower the intrinsic viscosity for a given degree of carboxylation. Because it is not known, a priori, what the final viscosity will be, the current method allows the continuous or substantially continuous measurements of intrinsic viscosity to be extrapolated into the future of the reaction to predict when the intrinsic viscosity will reach a given value, such as a desired set-point value, and what the final value of intrinsic viscosity will be when the reaction reaches completion. Intrinsic viscosity is often a chief specification for a polymeric product, and the presently disclosed technology can ensure that the specification is reached. The method can similarly be applied to the electrical conductivity in the latter case. For example, the free $OH^-$ ions of NaOH in solution suffer a decrease in electrophoretic mobility when they are incorporated into a charged carboxylate group on the polyacrylamide. It is unknown, however, what the final decrease in solution conductivity will be, since the change of free to bound $OH^-$ decreases electrophoretic mobility but does not eliminate it. Hence, the continuous or substantially continuous conductivity can be extrapolated to the endpoint, so that the degree of carboxylation can be determined at each instant, where the initial concentrations of NaOH and polyacrylamide are known.

Similarly, when charged comonomers are involved in copolymerization with uncharged monomers there is also a reduction in electrophoretic mobility, and hence solution electrical conductivity, when the charged monomer passes from being a free monomer in solution to being a link in the polymeric chain. The change in conductivity is, a priori, unknown, but the presented method allows extrapolation of the continuous or substantially continuous conductivity data to predict the remaining concentration of charged monomer. Combined with a measure of the other comonomer's or comonomers' concentration, such as from simultaneous independent spectroscopic measurements, the composition of the polymer chains at every instant can additionally be determined.

FIG. 1 is a diagram of an exemplary polymerization reaction process control and monitoring system 100 for controlling the properties of chemical species during time-dependent polymerization processes. The control system 100 includes an ACOMP reactor control interface 101 and an ACOMP analysis control interface 102. In at least one embodiment, the ACOMP reactor control interface 101 and the ACOMP analysis control interface 102 are controlled by a Programmable Logic Controller (PLC) control system (not shown) which is coupled to a computing device (not shown). The PLC control system can be, for example, an Allen Bradley/Rockwell ControlLogix PLC control system (Rockwell Automation, Inc., Milwaukee, Wis., USA). The computing device can be a desktop or laptop computer, a smartphone, a tablet, or any other similar device. The computing device can allow for visualization and control of process control variables and components of the control system 100.

The ACOMP reactor control interface 101 can control various components of the control system 100. One component is a reactor 110. The reactor 110 can be a 1.5 Lm 316-L stainless steel jacketed reactor with a 6 port, bolt-on lid (not shown) that allows for the attachment of process feeds such as monomer, initiator, catalyst, quencher, cross-linking or branching agent, or chain transfer agent, as discussed below. The reactor 110 can be any one of a batch reactor, a semi-batch (or semi-continuous) reactor, or a continuous reactor. A submersible stainless steel temperature probe (not shown) can be attached through the top of the reactor lid so that temperature of the reactor contents may be accurately monitored and controlled. The reactor lid can allow for the attachment of a mixer 140. The mixer 140 is located outside of the reactor 110. The mixer 140 can be, for example, an IKA Eurostar overhead mixer (IKA® Works, Inc., Wilmington, N.C., USA).

An impeller coupling (not shown) can be attached to the mixer 140. The impeller coupling can be, for example, a Buchi Glass Mag Drive impeller coupling (Biichi AG, Uster, Switzerland). The impeller coupling can connect to a 4 blade stainless steel impeller inside of the reactor 110 and provide agitation.

Flow controllers 120, 122 can be used for the addition of gases into the reactor 110. Gases added via the flow controllers 120, 122 can be, for example, nitrogen, oxygen or air. Flow controllers 120, 122 can be, for example, MKS Gas Flow Controllers (MKS Instruments, Inc, Andover, Mass., USA). Each flow controller 120, 122 can have an inlet (not shown) coupled with a regulated gas cylinder. Each flow controller 120, 122 can be rated for to have an inlet pressure of 100 pounds per square inch (PSI). Each flow controller 120, 122 can have an outlet (not shown) connected the reactor lid. Gas can be preciecsly dispensed by a dip tube (not shown) into the reactor 110 through the inlet. Gases can be dispensed to the reactor 110 at a rate ranging from about 20 sccm to about 1000 sccm.

Pumps 130, 132, and 134 can be used for the addition of solutions or liquids to the reactor 110. The solutions or liquids can be, for example, one or more monomers, one or more initiators, catalyst, quencher, crosslinking or branching agent, chain transfer agent, a solvent, fluids for colloidal suspensions or any other suitable solution or liquid for use in a polymerization reaction process. It is also possible to use other dispensing means into the reactor 110, such as devices for dosing in solids or powders, such as salts. Pumps 130, 132 and 134 can be, for example, reciprocating piston pumps as provided by Fluid Metering Inc. (Syosset, N.Y., USA). Pumps 130, 132 and 134 can allow for precise control of the volumetric flow of solution or liquids being fed into the reactor 110. The volumetric flow can be, for example, rates from about 0.1 ml/min to about 20 ml/min. Pumps 130, 132 and 134 can be reversible such that they can also be used to extract contents, such as reagents or other chemical components or polymerization reaction process products, from the reactor 110.

The reactor 110 and contents contained therein can also be subjected to heating or cooling from a temperature controller 138. The temperature controller 138 can transfer heat to the reactor 110 and contents contained therein vie a jacket (not shown). The jacket can be permanently or reversibly connected to one or more external surfaces of the reactor 110. The jacket of the can be coupled with a temperature controlled circulating bath (not shown). The submersible temperature probe, as mentioned previously, can be used to complete a feedback loop which accurately maintains the desired temperature of the reactor 110 and contents therein. The inlet and outlet temperature of the reactor jacket can each be monitored by a thermocouple (not shown) for use in calorimetric heat transfer calculations.

The reactor 110 is also coupled with a recycle pump 150. The recycle pump 150 can be coupled with a bottom portion of the reactor 110 via a drain port (not shown) and ball valve (not shown). Reactor contents can be continuously extracted through the recycle pump 150 and recycled back into the top of the reactor 110. The reactor contents can be pumped through a recycle line (not shown) comprising, for example, 1/8" OD stainless steel tubing. The reactor contents can be pumped at a rate of 20 ml/min. Alternatively, the reactor contents can be pumped at a rate ranging from, for example 5 ml/min to 50 ml/min, alternatively 10 ml/min to 40 ml/min, and alternatively 15 ml/min to 30 ml/min. An extraction point along the recycle line can be used to sample a small stream of the reactor contents for conditioning and analytical measurement by the ACOMP system interface 102. The recycle pump 150 can be an internal gear pump such as a Zenith Pump (Colfax Corporation, Annapolis Junction, Md., USA). The internal gear pump can have a displacement of, for example, 0.1 cc per revolution. The recycle pump 150 can be made of hardened tool steel and be rated for viscosity ranges of 1-2M centipoise.

An extraction pump 160 connects the ACOMP system interface 102 to the reactor control interface 101 via the recycle pump 150 can be, for example, reciprocating piston pumps as provided by Fluid Metering Inc. (Syosset, N.Y., USA). The volumetric flow of the extraction pump 160 can be, for example, rates from about 0.2 ml/min to about 2 ml/min. The extraction pump 160 can pump in both forward and reverse directions.

The extracted reactor contents are combined with a flow of quenching solvent from a solvent source 168. The extracted reactor contents and solvent can be combined at a ratio of, for example, 10/1. This purpose of the quenching solvent is to halt propagation of the polymerization reaction process. Mixing and dilution processes reduce the concentration of extracted reactor contents to allow for more accurate measurement of single molecule intrinsic properties. Once the reactor contents are combined with the quenching solvent. The combination can be passed by inert propylene tubing (not shown) to a dynamic mixing chamber 170. The mixing chamber 170 can be used to actively stir and combine the two continuous streams of reactor contents and solvent into one homogenous mixture. The volumetric amount and agitation/stirring rate of the mixing chamber 170 can be pre-determined and customized according to the polymerization reaction process or corresponding characteristics. Occasionally in cases of extremely high reactor concentrations, there can be a need for additional mixing or further dilution. In such instances, an additional mixing chamber (not shown) and secondary solvent, from a secondary solvent source (not shown), can be used to further reduce the concentration of the reactor contents for single molecule measurement.

After the homogenous solution leaves the mixing chamber 170, it is passed through a filtration system 172 to remove any particulate or gel matter that may have been removed from the reactor 110 with the reactor contents. In one non-limiting example, filtration system 172 is a 40 μm stainless steel mesh filter. The type of filtration system 172 is not limiting in any way and can be changed depending of the particular polymerization reaction process or characteristics thereof.

The filtered homogeneous solution can then be flowed through one or more inline analytical detectors 174. One or more inline analytical detectors can be called a "detector train." In one example, the detector train can include a UV/Visible absorption spectrometer and a temperature controlled single capillary viscometer. The UV/Visible absorption spectrometer can continuously monitor up to four (4) independent wavelengths and have a 0.2 cm path length cell capable of accommodating flow rates up to 50 ml/min, such as for example a UV/Visible absorption spectrometer from Gilson, Inc. (Middleton, Wis., USA). The UV absorption of the homogeneous solution can be directly correlated, for example, to the concentration of monomer in the reactor contents and to the concentration of polymer produced as monomer is consumed throughout the polymerization. The single capillary viscometer is designed for monitoring the differential change of pressure across the capillary due to the increase or decrease of viscosity of a steady flow of solution. This measure of viscometric pressure along with the concentration determined from the UV/Vis detector allows for the absolute measure of intrinsic/reduced viscosity of the polymer being produced. This single capillary viscometer was developed and produced by Advanced Polymer Monitoring Technologies Inc.

The analysis procedures handled by the ACOMP analysis control interface 102 include the interpretation of raw UV/Vis absorption and viscometric pressure to determine the process characteristics such as monomer concentration, polymer concentration, total process conversion, and intrinsic/reduced viscosity. The automated method of this interpretation is handled by an on board analysis package 176 that responds to manual operation triggers through interface with Automation and Control software. These triggers instruct the analysis software to perform key analysis algorithms appropriate to each step or phase in the polymerization reaction process.

A process controller 180 can be coupled with the ACOMP reactor control interface 101 and the ACOMP analysis control interface 102 to provide a means to which the user can interact with the ACOMP reactor control interface 101 to perform operations that will directly influence the propagation of the polymerization reaction and view data obtained from the ACOMP analysis control interface 102.

The following embodiment is an illustration only of the principle of the technology and is not meant to be limiting. Consider the copolymerization reaction of acrylamide and a comonomer (for example, styrene sulfonate, vinyl pyrrolidone, acrylic acid, or any other suitable comonomer). It does not matter if the reaction is of the free radical, controlled radical, or other type, or whether it occurs in a homogeneous solution or in an inverse emulsion or other heterogeneous phase.

The application of the technology here is to follow residual acrylamide monomer down to a specified concentration on a parts per million (ppm) scale. UV absorbance can be chosen as a means to accomplish such residual chemical detection on a ppm scale. Other means of measuring residuals in a continuous fashion include absorbance measurements in other parts of the electromagnetic radiation spectrum, such as in the infra-red region, Raman scattering, fluorescence, refractometry, and conductivity, among others.

The kinetic approach to residual ppm determination has the advantage of avoiding any recourse to interpreting UV signals of each component in terms of extinction coefficients, which can vary from batch to batch, or by using 'UV self-calibration'. The 'absorption' readout of the UV detector is actually the combination of both molecular electronic absorption and UV light scattering. The latter is particularly prone to variations. For example, the UV light scattering at any given wavelength by copolymer in a dilute solution flowing through the detector train depends not only on the copolymer concentration, but also on its molecular weight, polydispersity, comonomer composition, and ionic strength of the aqueous medium. Also, of possible concern is extra scattering produced by microgels and other particulates, when they are present. Furthermore, extinction coefficients (composed of both the absorption and scattering effects) of the various chemical components, such as comonomers, surfactant, initiators, copolymers, oil droplets, and so on, can vary for identical materials from run-to-run due to variations in product quality and within the accuracy and precision limits of the UV detectors used.

The UV "absorbance" at any wavelength $\lambda$, $A(\lambda)$, which includes both absorbance and scattering, is measured by the decreased intensity, $I(\lambda)$, passing through an absorbing medium from an incident intensity $I_o(\lambda)$, according to $$I(\lambda) = I_o 10^{A(\lambda)} \qquad (1)$$

where $$A(\lambda) = L \sum_{i=1}^{N} c_i(t) \varepsilon_i(\lambda) \qquad (2)$$

Here, the sum is over N different absorbing/scattering species, L is the path length of the UV cell, $\varepsilon_i(\lambda)$ is the extinction coefficient (sum of absorbance and scattering) of species i at wavelength $\lambda$, and $c_i(t)$ is the concentration of species i, which may be time dependent. For example, in the case of a polymerization reaction i=1 could be a monomer species, which decreases in time, and i=2 could be a polymer species which increases in time, i=3 might be an initiator or catalyst concentration which could stay constant or vary only slightly in time, and so on.

Because of the time dependence of the species in polymerization reactions, kinetic approaches are desirable over "static" approaches that use extinction coefficients of the various components. Two kinetic approaches are presented herein.

One kinetic approach exploits the continuous signal available from an ACOMP system for acrylamide (Am) conversion, and can use a functional fit, such as first order, or an empirical form, to predict when the target concentration or amount of residual Am, or "ppm setpoint," will be reached. Because of the continuous availability of the data, the estimated time to approach can be continuously updated and more precisely computed as the reaction approaches the target. The technology is not limited by the form of the fit. Any analytical, numerical, spline, interpolative, smoothing, transform fit, or other suitable fit can be used that suits the data of any particular application.

An example of this would be to use first order kinetics so that the concentration (in ppm) of Am in the reactor as a function of time ppm(t) at any given wavelength is expressed as:

$$ppm(\lambda, t) = \frac{D[A(\lambda, t; t_{r1}, t_{r2}) - P(\lambda; t_{r1}, t_{r2})]}{\varepsilon_{Am}(\lambda) L} \qquad (3)$$

where $t_{r1}$ is the first reference time at which the fitting starts, $t_{r2}$ is the second reference time at which the fitting ends, and t is any time for which $t > t_{r1}$, including time projection out to and beyond the ppm setpoint. D is the dilution factor from the reactor to the UV detector, 1 is the UV cell path length, $\varepsilon(\lambda)$ is the extinction coefficient of Am, and $P(\lambda, t_{r1}, t_{r2})$ is the plateau value to the UV signal at the projected end of the reaction. For example a first order fit over $t_{r1}$ to $t_{r2}$ is expressed as follows:

$$A(\lambda, t; t_{r1}, t_{r2}) = A(\lambda, t_{r1}, t_{r2}) e^{-\alpha(t - t_{r1})} + P(\lambda, t_{r1}, t_{r2}) \qquad (4)$$

This involves fitting three parameters over the time interval $t_{r1}$ to $t_{r2}$: $\alpha$ is the fitted rate constant, $P(\lambda, t_{r1}, t_{r2})$ is the fitted plateau and $A(\lambda, t_{r1}, t_{r2})$ the fitted absorbance at $t = t_{r1}$.

This approach rests on the assumption that $P(\lambda, t_{r1}, t_{r2})$ represents UV absorption from all remaining, non-changing chemicals in the reactor at the end of the reaction. Due to the fact that it is a constant value, the net UV absorption when all Am with intact double bonds has been used is indicated. This fundamental assumption has been cross-checked with high pressure liquid chromatography (HPLC), a standard separation method for determining residual chemical species, and definitive agreement has been found. That is, the concentration predicted by the kinetic method is in good agreement with the conventional HPLC method, as seen in Table 1. Table 1 displays results from multiple Am polymerization experiments monitored using an ACOMP system and HPLC instrument respectively. The time, in seconds, from the beginning of acrylamide polymerization reactions until the 500 ppm level of Am is reached. The ACOMP column shows the results of the prediction using the above described kinetic method, the second column shows the result from conventional HPLC on reaction aliquots withdrawn manually at intervals.

TABLE 1

| Reaction Trial | Average Time (sec) Using ACOMP | Average Time (Sec) Using HPLC |
|---|---|---|
| 1 | 2757 | 2750 |
| 2 | 2327 | 2300 |
| 3 | 2733 | 2375 |
| 4 | 2257 | 2750 |
| 5 | 2880 | 2750 |
| 6 | 6410 | 6550 |
| 7 | 4450 | 6250 |
| 8 | 5234 | 5940 |

Figure 2:
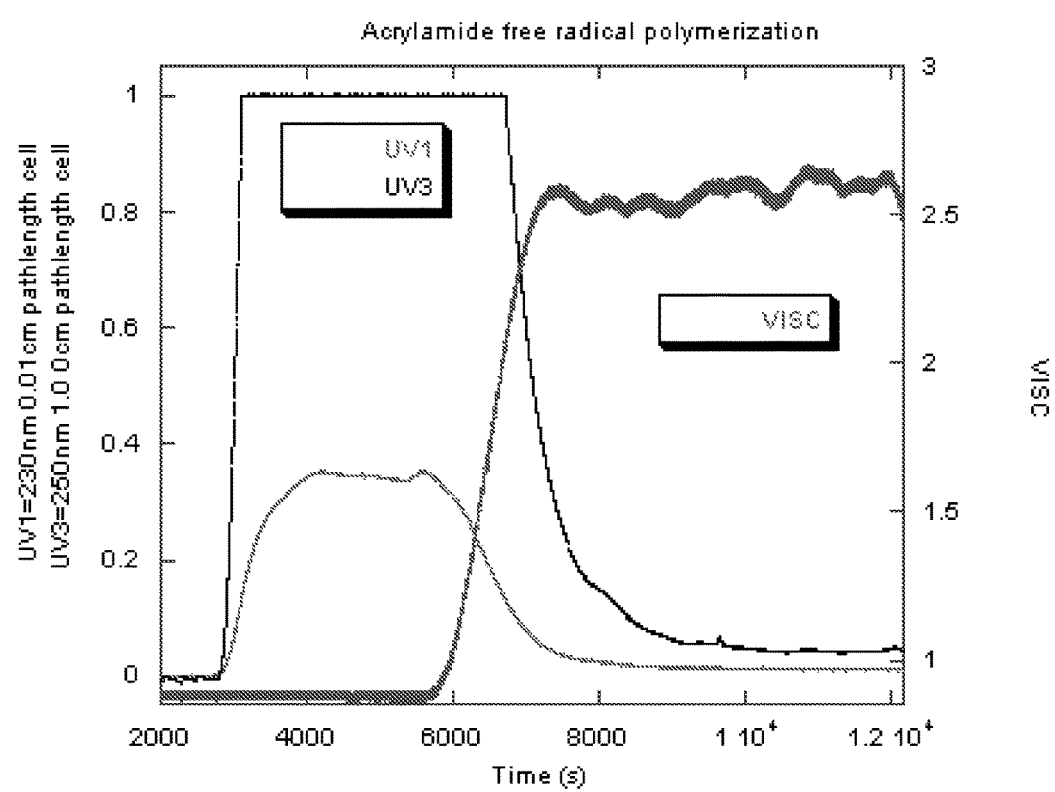
FIG. 2 is a graphical display of ACOMP data from an acrylamide (Am) polymerization with acrylic acid in accordance with an exemplary embodiment of the present disclosure.

FIG. 2 is a graphical display of ACOMP data from an acrylamide polymerization with a small amount of acrylic acid. The concentration of combined monomer and polymer in the detector stream issuing from the ACOMP dilution/conditioning portion was $8.3 \times 10^{-4}$ g/cm$^3$. Besides two UV wavelengths the raw viscosity signal from the dilute solution is also shown, from which the reduced viscosity of the polymer is determined. The VISC signal is a continuous signal corresponding to the intrinsic viscosity of the polymer. The interest here is to follow the monomer ppm down to low values, both predicting when ppm levels will be reached, and announcing the latest ppm level.

UV detector #1, UV1, has a 0.01 cm path length cell and is set to monitor a wavelength of 230 nm. UV detector #3, UV3, has a 1.00 cm cell and is set to monitor a wavelength of 250 nm. Alternatively, one UV detector with a path length between, for example, 0.2 cm, can be used if the proper wavelengths are selected. Some UV spectrometers remain linear up to high levels of absorption, which can also facilitate the use of a single spectrometer, and even a single wavelength when comonomer separation analysis is not required. Because the absorbance A in equation 2 is proportional to path length L, changing the path length by 100× in UV3 compared to UV1 increases the signal by 100×. Hence, in this particular case UV1 can measure the bulk of the polymerization down to about 98%, whereas UV3 remains saturated until the reaction is about 62% complete, after which it desaturates and gives a strong signal. The use of two UV detectors with different path lengths is not limiting, since it is possible to use two different wavelengths on the same detector, one of which will be below saturation during the majority of conversion and the other desaturates in the later stages of conversion. The use of two wavelengths is also not limiting since a single wavelength can also be used in a detector with sufficiently low noise (e.g. GE UV, Knauer). Hence, a single wavelength UV absorbance instrument of sufficiently stable, low noise signal can be sufficient for use.

Figure 3:
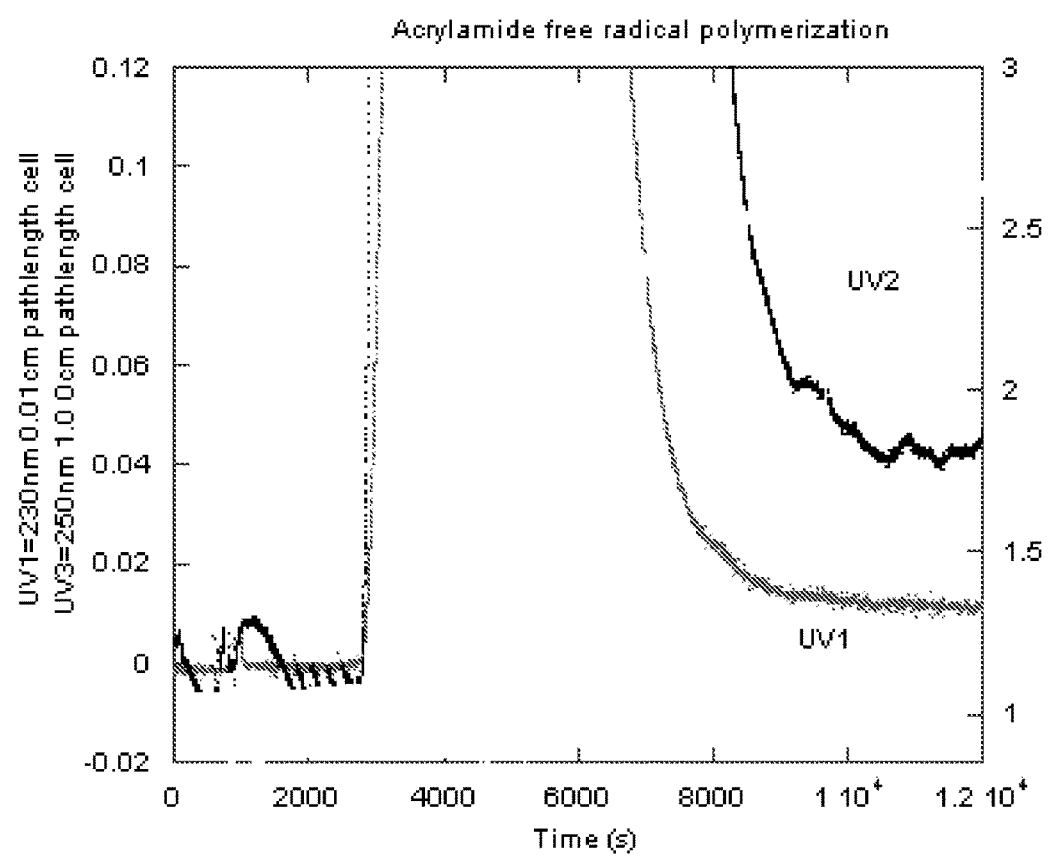
FIG. 3 is a graphical display illustrating the determination of low levels of residual monomer using a typical static method.

FIG. 3 is a graphical display illustrating the essential problem in trying to determine low levels of residual monomer using the typical static method. The baselines of both UV1 and UV3 at the end of the reaction are well above their initial solvent levels at the beginning of the reaction. In fact, using the static method (and the calibration factors 0.0024 g/cm³-Volt for UV1 and 3.1×10⁻⁴ g/cm³-Volt for UV3) would yield the erroneous results that there are 9,120 ppm in the reactor by UV1 and 4,560 ppm in the reactor by UV3.

This is far above the real level, cross-checked by HPLC to be ppm~500. This is due to absorption and scattering by the polymers and other species present in the reactor and in the diluted ACOMP stream.

Figure 4:
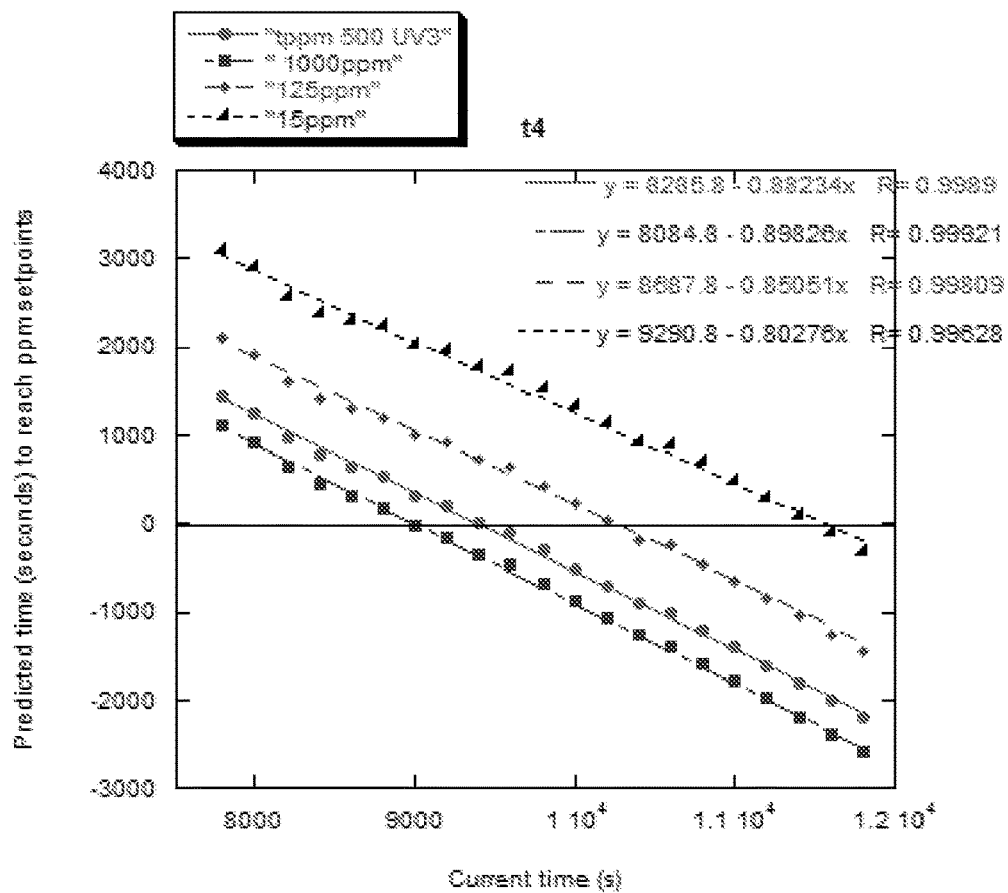
FIG. 4 is a graphical display illustrating predicted times to reach concentration setpoints vs. the time at which the prediction was made in accordance with an exemplary embodiment of the present disclosure.

FIG. 4 is a graphical display illustrating predicted times to several ppm setpoints, on the y-axis, versus the time at which the prediction was made. The results are from a computer program written by the inventor. The extrapolations use ACOMP data obtained from the free radical polymerization of acrylamide in inverse emulsions in a continuous oil phase. A single decaying exponential with amplitude, a, rate, α, and baseline b, were the three fit variables. The exponential is of the form according to equation (4), which was also given above as:

$$A(\lambda,t;t_{r1},t_{r2}) = A(\lambda,t_{r1},t_{r2})e^{-\alpha(t-t_{r1})} + P(\lambda,t_{r1},t_{r2})$$

where the fit occurs over the interval $t_{r1}$ to $t_{r2}$, $A(\lambda,t_{r1},t_{r2})$ is the absorbance at $t_{r1}$ due only to the changing monomer concentrations. The fit value of $P(\lambda,t_{r1},t_{r2})$ takes account of the change in $P(\lambda,t_{r1},t_{r2})$ due to other species at the time of each new fit; in this case $P(\lambda,t_{r1},t_{r2})$ changes in time due to increased scattering from acrylamide polymer produced during the reaction. The fitting interval is from $t_{r1}$ to $t_{r2}$, where $t_{r2}$ is the most recent time the calculation is repeated. The $t_{r1}$ can change upon successive fits or remain constant, depending on the quality of the fit over the interval. The latter was applied in FIG. 4. The time (t) at which a desired A, and hence any desired ppm setpoint occurs can be found by solving the above equation for time (t). Negative values mean the setpoint has been passed and the reaction is at lower concentration than the setpoint.

Another form that can be used for fitting, which is not limiting, is the use of the Gaussian (or Normal) function. This function can occur in reaction kinetics under several conditions such as i) when there is a continuous feed of initiator into a reactor, ii) a rise in temperature during the reaction, or a combination thereof, and other effects wherein the free radical concentration increases. Another case, which is described by an exponential of an exponential function occurs when the free radical concentration decreases during the reaction such as, for example, in a batch reaction where a thermal initiator, such as a peroxide or a persulfate, decomposes significantly during the reaction.

Another use for the fitting procedures used herein is when reactions follow well defined analytical functions when the reaction occurs as expected. For example, for free radical reactions in the quasi-steady state approximation, initiator decomposes slowly and a first order (exponential) conversion of monomer occurs. As mentioned, a constant flow of initiator into a free radical reaction results in a Gaussian (or Normal) function. See Dotson, N. A.; Galvan, R.; Laurence, R. L. and Tirrel, M., Polymerization Process Modeling 1996, VCH Pub., New York.

In the case of the ppm issue discussed here, the process controller can make predictive computations needed to both predict how long it will take to reach the ppm setpoint at any given time, and also signals when the setpoint is reached. Once this setpoint is reached and the process controller signals this event a number of actions can be taken by the process controller. For example, when the ppm setpoint is reached, the process controller can change the temperature of the reactor to cool and the contents can then pumped into a storage vessel, such as an onsite tank, or a railroad tank car. In other cases, the process controller can control the addition of a quenching agent, such as oxygen or other agent(s), to the reactor and cooling and product removal from the reactor later ensue. In other cases it may not be necessary to either quench or cool the reactor and the process controller can control product removal immediately upon reaching the setpoint. In other cases, the process controller can initiate a secondary stage of a reaction in the same reactor, such as by controlling the addition of a crosslinking or branching agent, and/or other monomers of the same or different type, or a polymer modification, such as hydrolysis or sulfonation may begin. In some cases, the process controller can initiate pumping or transferal of the reactor product into a different reactor for one or more subsequent reactions. No matter what the specific sequence of actions, the process controller signals when the sequence of actions should begin and the sequence may be carried out manually, by reactor operators or other personnel, or automatically by the process controller itself, which can be equipped to actuate heating and cooling cycles, actuate pumps for introducing and removing content from the reactor, etc.

In contrast, without the current technology, it is standard practice in industrial production to manually take samples from the reactor, bring them to a quality control lab, and then perform an analysis, such as high pressure liquid chromatography analysis (HPLC) for ppm of monomer. This manual sampling is very inefficient and time consuming, typically taking from 45 minutes to two hours or more to obtain sample and an analytical result. The current technology, operating continuously and automatically, completely avoids the need for intermittent, inefficient manual sampling, and delivers the ppm setpoint signal in near realtime. In 'near realtime' means that there is a delay between automatic extraction, dilution and conditioning of the continuous reactor sample and the continuous analytical measurements. This delay is typically between 30 seconds and five minutes, which is far less than manual sampling cycles, less labor intensive, and eliminates the need to expose workers to an often dangerous reactor environment.

The example above where ppm setpoint is used is not limiting. Meeting a ppm setpoint is common in many polymer manufacturing operations, including, but not limited to, those involving styrenics, acrylates, methacrylates, ethacrylates, carbonates, sulfones, olefins, vinyl chlorides, vinyl alcohols, fluorinated monomers, imides, urethanes, and many others.

The use of ppm as the setpoint if also not limiting. In some processes, for example, a specific molecular weight of a polymer product made in a time-dependent process is the setpoint. The device which continuously extracts, dilutes, conditions and analyzes reactor content in near realtime can provide predictions of the molecular weight trajectory in time—either a molecular weight average, such as the weight average molecular weight from light scattering, or the viscosity averaged molecular weight from viscometry, or full molecular weight distributions—which serves as the setpoint indicator. Once the molecular weight setpoint is reached, as computed by and signaled by the process controller, then specific actions can be taken by the process controller. These include, but are not limited to, stopping the reaction and collecting the contents, or proceeding to a subsequent reaction stage either in the same or another reactor. Subsequent reaction stages, of which there can be one or more, and which can occur in the same or one or more separate reactors include, but are not limited to, producing subsequent blocks of block copolymers, using different catalysts, initiators, or agents to achieve higher molecular weight, lower molecular weight or multimodal molecular weight distributions, crosslinking, or branching, or functionalizing. Functionalization can include, but is not limited to, hydrolysis by acids or bases, enzymatic treatments, sulfonation, amination, carboxylation, hydroxylation, PEGylation, and others. The current technology can be used to monitor these subsequent stages to determine when the respective setpoints are reached and to signal these, upon which signal any sequence of actions can be carried out, either manually or by the process controller itself.

Besides the case of monitoring desired molecular weight increases or decreases, or functionalizations in the secondary stages, the current technology also allows monitoring for undesirable products and reactions. As a non-limiting example, a chemical treatment after a previous stage may lead to both beneficial increases in a property, such as acquiring functional groups on the polymer, but simultaneously lead to undesired effects, such as loss of polymer molecular weight or intrinsic or reduced viscosity. The process controller can monitor both the beneficial and detrimental effects and signal when the desired amount of beneficial effect is achieved, as balanced against detrimental effects.

The use of residual ppm and molecular weight are not limiting as regards setpoints. Other setpoints can include reaching a given level of monomer conversion, reduced or intrinsic viscosity, composition of copolymers, polydispersity, and other characteristics. Reaching these setpoints may lead to stopping the reaction and collecting the product, or proceeding to subsequent stages. In all cases the process controller can signal, via computations from the continuously supplied monitoring data, when the various setpoints are reached, allowing subsequent sequences of actions to be carried out manually or automatically by the process controller.

While the above examples have centered on synthetic polymers the current technology can be used for the manufacture of natural product derived products. For example, it is common practice to derivitize polysaccharides, such as galactomannans, gums such as guar and gum Arabic, alginates, carrageenans, xanthans, scleroglucans and many others, either chemically or enzymatically. These derivitizations are carried out to provide the starting material with desired endproduct characteristics, such as desired viscosity, solubility, ability to form nano- and microstructures, molecular weight, and hybridization with other materials, such as synthetic polymers. In these cases the process controller can monitor the desired properties, compute their time courses, and signal when desired characteristics are reached. When the desired characteristics are reached, as signaled by the process controller, and desired sequence of subsequent actions, such as reaction stoppage and storage, and further reaction or treatment stages can be carried out manually or automatically by the process controller.

As discussed above, polymers consisting of two or more comonomers, usually termed "copolymers," are frequently of interest. In such cases it may be of interest to separate the concentrations (directly related to conversion) of the two or more comonomers, and apply the kinetic method to one or more of the comonomers. Methods for using two or more wavelengths have been presented for separating conversion of multiple monomers (for example, see A. M. Alb, P. Enohnyaket, M. Drenski, A. Head, A. W. Reed, W. F. Reed, "Online monitoring of copolymerization using comonomers of similar spectral characteristics", Macromolecules, 39, 5705-5713, 2006). The presently disclosed technology allows for the use of one or more of these multiple wavelength determinations for comonomer concentrations, within the kinetic context, for kinetic determination of residual monomer concentration of each monomeric species.

In the latter case one is not constrained to using multiple wavelengths to separate monomer concentrations during a reaction. It has been previously demonstrated, as a non-limiting example, that a refractometer in conjunction with a single UV wavelength can be used to separate concentrations of styrene and methyl methacrylate during polymerization reactions (A. Giz, A. Oncul Koc, H. Giz, A. M. Alb, W. F. Reed "Online monitoring of reactivity ratios, composition, sequence length, and molecular weight distributions during free radical copolymerization", Macromolecules, 35, 6557-6571, 2002). In this case, the kinetic method of the current invention can be used to monitor residual monomer concentration of either or both monomers.

Yet another means of obtaining comonomer concentrations, when one of the comonomers is electrically charged (for example, acrylic acid, quaternized acrylamide, styrene sulfonate, and so on) involves use of one or more UV wavelengths and a conductivity monitor. The conductivity will be responsive only to the conversion of the charged comonomer to a polymer, so that the kinetic approach of the current invention could be used to monitor residual charged comonomer concentration from the conductivity signal, whereas the one or more UV wavelengths could be used to kinetically follow residual monomer of one or more uncharged comonomers. For example, the use of UV and conductivity to monitor the copolymerization of acrylamide (electrically neutral) and styrene sulfonate (negatively charged) has been reported (A. M. Alb, A. Paril, H. catalgil-Giz, A. Giz, W. F. Reed, "Evolution of composition, molar mass, and conductivity during the free radical copolymerization of polyelectrolytes", J. Phys. Chem. B, 111, 8560-8566, 2007).

Another example are "living" type reactions, such as controlled radical polymerizations (of the sorts ROMP, RAFT, ATRP, NMP, anionic, cationic, and others). In "living" polymerization reactions, the molar mass of the polymer increases linearly with conversion. In the same type of reaction with first order conversion the molar mass of the polymer follows an increasing, parabolic trajectory.

For analytical functions, or numerical functions that are found to correspond to certain types of reactions, these can provide a guide for controlling the polymerization reaction. Namely, if a time dependent signature of a reaction—for example, conversion of monomer, molar mass, reduced viscosity, polydispersity, chirality, optical activity, pH, or conductivity—is associated with the way in which the reaction should proceed, then the monitored signature can be compared to the expected signature and changes in reaction control procedures made in order to ensure that the reaction follows the expected signature. Such process control operations can be carried out either manually or automatically using an active interface between the analysis and the process control actuators such as, for example, a feedback loop.

The presently described technology can be used in homogeneous phase, bulk phase, or heterogeneous phase free radical reactions. The presently described technology can also be used in homogeneous phase, bulk phase, or heterogeneous phase controlled radical reactions. Additionally, the presently described technology can be used in homogeneous phase, bulk phase, or heterogeneous phase step-growth reactions. The reactions can also be batch reactions, semi-batch reactions, or continuous reactions.

Figure 5:
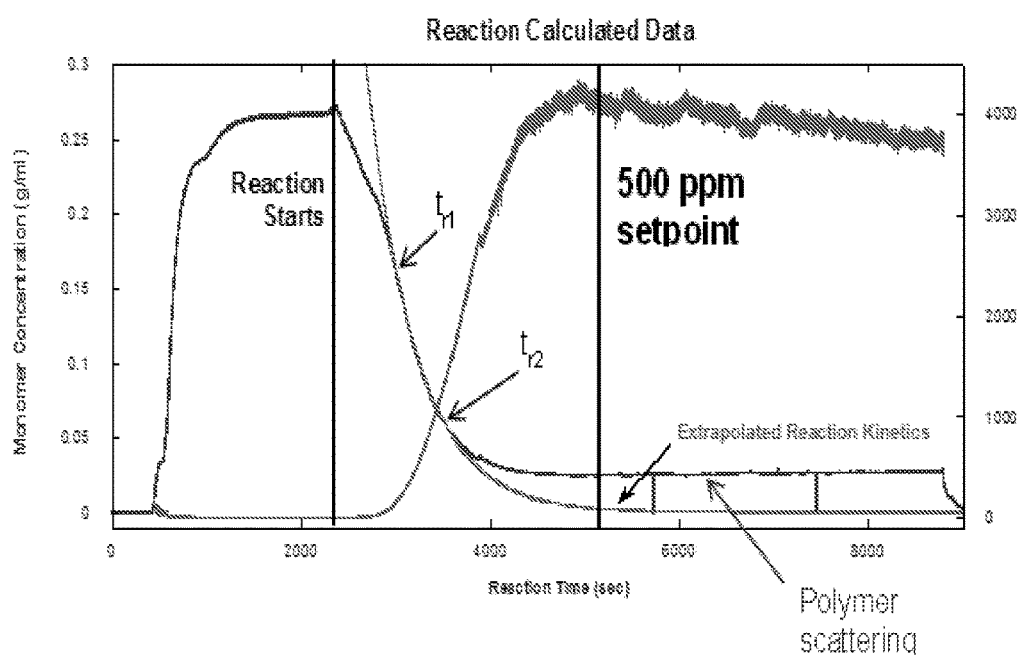
FIG. 5 is a graphical display illustrating another Am polymerization reaction where the kinetic method can be used to determine an Am concentration setpoint is reached in accordance with an exemplary embodiment of the present disclosure.

FIG. 5 is a graphical display illustrating another acrylamide polymerization reaction where the kinetic method is used to determine when the 500 ppm Am setpoint is reached. FIG. 5 displays the time limits used, $t_{r1}$ and $t_{r2}$, as well as the extrapolated Am concentration.

There is no fundamental lower limit on the ppm setpoint that can be determined by this kinetic approach. For example, FIG. 4 shows predicted times down to a 15 ppm setpoint, but there is no reason this could not be extended to concentrations below 1 ppm, or even concentrations down to 1 ppb (part per billion) or lower, since there is no upper limit on the time to which the fit can be extrapolated. Such extrapolations to very low ppm or ppb concentrations, or lower, can be useful for products that are stringently regulated, such as chemical products for human use, or for polymeric products used in exacting applications, such as optics and electronics, where monomers and other residuals must be in the ppb or lower concentration range.

Figure 6:
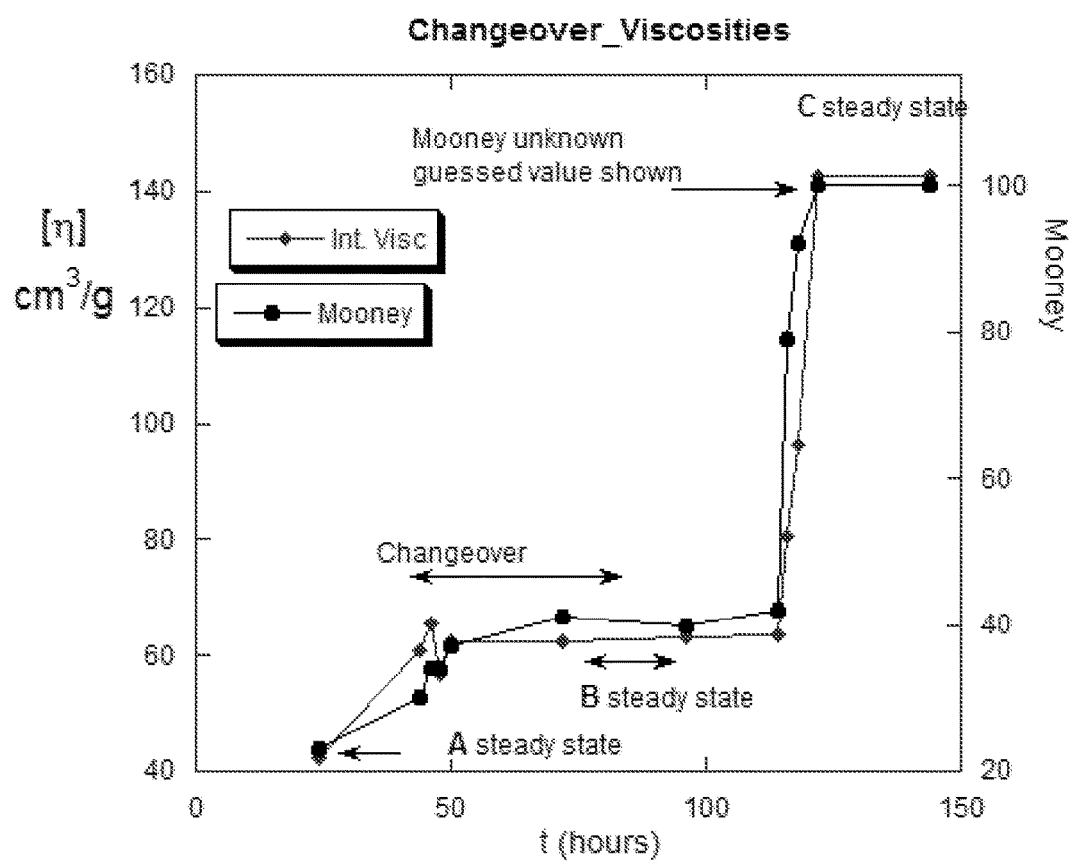
FIG. 6 is a graphical display illustrating discrete points marking polymer grade changeover using offline reduced viscosity measurements and offline Mooney Viscosity measurements in accordance with an exemplary embodiment of the present disclosure.

Consider the grade changeover from one type of polymer to another in a continuous reactor. FIG. 6 is a graphical display illustrating discrete points marking grade changeover using offline reduced viscosity measurements and also offline Mooney Viscosity measurements, an industry standard rheological measurement used in the synthetic rubber manufacturing industry. If online data were available from a suitable detector, e.g. a viscometer, it would be possible to apply the presently disclosed technology to predict when the new grade is reached in real-time. A similar method as in the previous example could be employed. The data could be fit to a function, for example a sigmoid function, and it could then be predicted when the changeover of grade is sufficiently complete to start collecting product.

Figure 7:
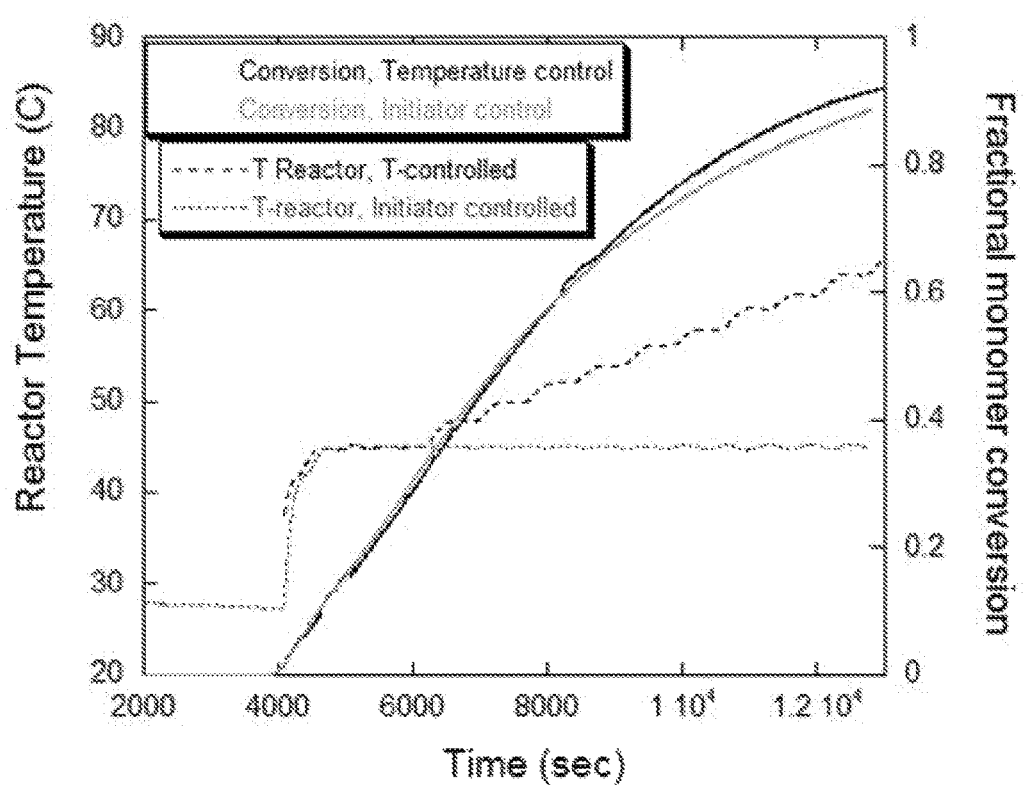
FIG. 7 is a graphical display illustrating an exemplary use of a process controller to change reaction conditions to follow the time course of monomer conversion in a free radical polymerization reaction.

The process controller of the device embodiment of FIG. 1 allows for control of the reactions by changing process conditions such as temperature, agitation, flow of reactants and reagents into the reactor, such as, but not limited to monomers, catalysts, initiators, crosslinkers, branching agents, quenchers, chain transfer agents, solvents, gases, and solids such as powders or pellets. FIG. 7 shows an example of the use of the process controller to change reaction conditions so as to follow the time course of conversion. In this case an acrylamide free radical polymerization was carried out first by incrementing the temperature, as seen in FIG. 7, at a fixed initiator concentration. In a second, isothermal reaction at T=45° C. the fractional monomer conversion versus time was made to follow the same trajectory as in the first reaction by manually actively controlling the flow of initiator into the reactor. This is termed a 'Conversion isomorphic reaction pair', meaning that the conversion trajectory for the two reactions is the same but is achieved through different process conditions. The current technology can combine this type of control with predictive functions to both steer the reaction to a desired set point, such as final conversion or residual monomer, and predict the time to arrival at the set point.

Figure 8:
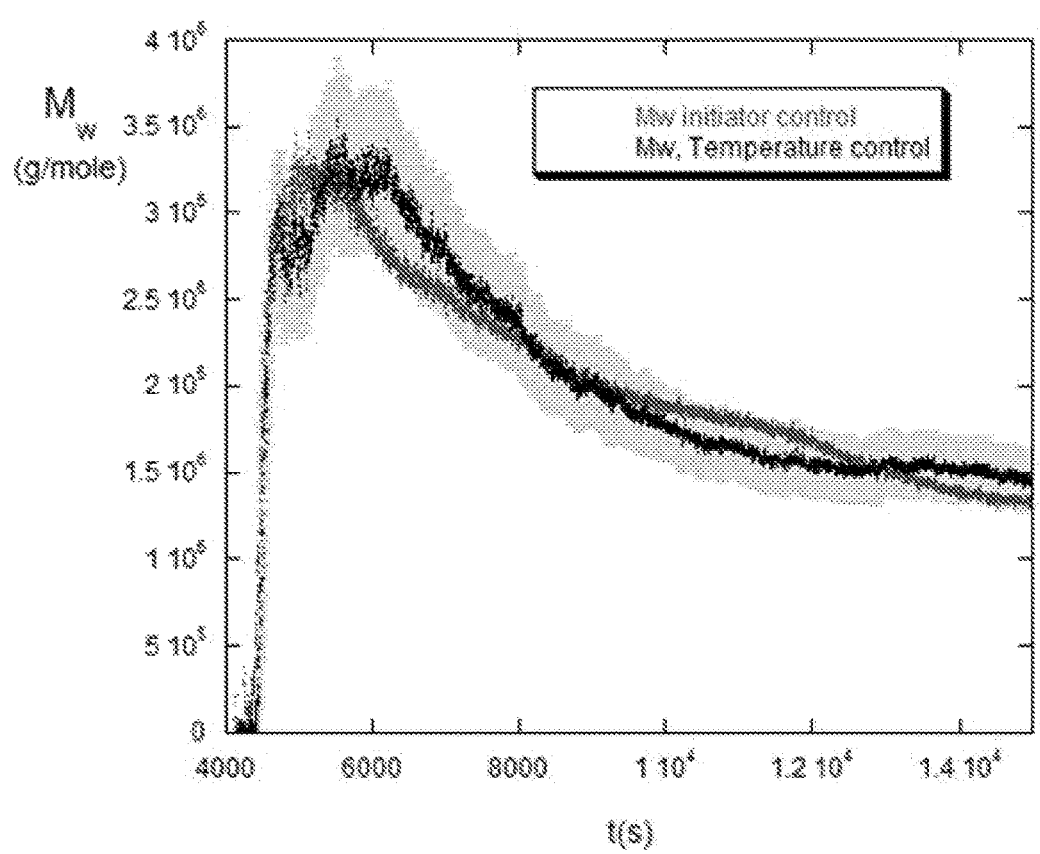
FIG. 8 is a graphical display illustrating a molecular weight isomorphic reaction pair.

Similarly, FIG. 8 shows a molecular weight isomorphic reaction pair, where the $M_w$ versus time trajectory for the first reaction was from the changing temperature reaction in FIG. 7. In the second paired reaction of FIG. 8, which was also isothermal at T=45° C., the initiator was actively manually controlled so that $M_w$ versus time followed the same trajectory as the first reaction where temperature was changed. The light grey swath of data points surrounding the $M_w$ initiator control and temperature control data is a 10% error bar. This active control capability, whether manually performed or automatically performed by the process controller, can be combined with the current predictive technology to enable the process controller to both steer the reaction along a desired trajectory such as, for example, within the 10% error bar, and predict when a given setpoint such as $M_w$, or a molecular weight distribution will be reached. Since the monomer to initiator ratio has different effects on conversion rate and $M_w$ the rate and amounts at which initiator was added in the second reactions of FIG. 7 and FIG. 8 were different.

STATEMENTS OF THE DISCLOSURE INCLUDE

Statement 1: A method comprising introducing, in a reactor, one or more chemical species to be monitored during a time-dependent process; detecting, using one or more detectors, one or more property changes to the one or more chemical species over a time interval; receiving, from the one or more detectors, a continuous stream of data related to the one or more property changes to the one or more chemical species during the time interval; fitting, using a process controller, the continuous stream of data to a mathematical function to predict one or more properties of the one or more chemical species at a future time point; and making, by the process controller, one or more process decisions based on the prediction of one or more properties at the future time point.

Statement 2: A method according to Statement 1, wherein the one or more process decisions comprise any one of terminating of the time-dependent process, recovering the reactor contents, proceeding to a subsequent reaction or processing stage in the same or a different reactor.

Statement 3: A method according to any one of Statements 1-2, wherein the time-dependent process is a chemical reaction.

Statement 4: A method according to any one of Statements 1-3, wherein the time-dependent process is a polymerization reaction.

Statement 5: A method according to Statement 4, further comprising fitting the continuous stream of data to a function to predict a grade changeover between a first polymerization reaction product and a second polymerization reaction product of the polymerization reaction, wherein one of the one or more detectors is a viscometer; and the predicted grade changeover is derived from reduced viscosity measurements detected by the viscometer during the time interval.

Statement 6: A method according to Statement 5, wherein the predicted grade changeover is derived from reduced viscosity measurements and correlated to offline Mooney Viscosity measurements.

Statement 7: A method according to any one of Statements 4-6, wherein the one or more property changes comprises changes in viscosity of a polymer product formed during the polymerization reaction.

Statement 8: A method according to any one of Statements 4-7, wherein the one or more property changes comprises changes in molecular weight of a polymer product formed during the polymerization reaction.

Statement 9: A method according to any one of Statements 3-8, wherein the one or more chemical species comprises one or more products of the chemical reaction.

Statement 10: A method according to any one of Statements 3-9, wherein the chemical reaction comprises any one of a free radical reaction in a homogeneous phase, a bulk phase, or a heterogeneous phase; a controlled radical reaction in a homogeneous phase, a bulk phase, or a heterogeneous phase; a step-growth reaction in a homogeneous phase, a bulk phase, or a heterogeneous phase; or a post-polymerization functionalization reaction.

Statement 11: A method according to any one of Statements 1-10, wherein the reactor is any one of a batch reactor, a semi-batch reactor, and a continuous reactor.

Statement 12: A method according to any one of Statements 1-11, wherein the one or more detectors is configured for measuring any one or more of UV absorption, infra-red absorption, Raman scattering, fluorescence, conductivity, reduced viscosity, dynamic light scattering, static light scattering, Mie scattering, evaporative light scattering, refractive index detection, linear birefringence, circular birefringence, linear dichroism, circular dichroism, infrared detection, NMR, and polarimetry.

Statement 13: A method according to any one of Statements 1-12, further comprising changing, using the process controller, one or more conditions of the time-dependent process to alter the predicted one or more properties of the chemical species at the future time point.

Statement 14: A method according to Statement 13, wherein the one or more conditions comprise any one of reactor pressure, reactor temperature, reaction stir rate, reaction agitation rate, reactant concentration, reagent concentration, or reagent flow rate into the reactor.

Statement 15: A method according to any one of Statements 1-14, wherein the one or more property changes comprise changes in any one of concentration, molecular weight, polydispersity, reduced viscosity, intrinsic viscosity, and chemical composition of the one or more chemical species.

Statement 16: A method according to Statement 15, further comprising predicting a time period required for a residual chemical species concentration to reach one or more specified levels.

Statement 17: A method according to Statement 16, further comprising changing, using the process controller, one or more conditions of the time-dependent process to alter the predicted residual chemical species concentration at a future time point.

Statement 18: A method according to any one of Statements 1-17, wherein the method is performed using an Automatic Continuous Online Monitoring of Polymerization reactions (ACOMP) system, the ACOMP system comprising the reactor, the one or more detectors and the process controller.

Statement 19: A device comprising a reactor for containing one or more chemical species of a time-dependent process; an extraction pump for automatically and continuously extracting an amount of the one or more chemical species from the reactor; one or more detectors for measuring property changes of the one or more extracted chemical species and generating a continuous stream of data related to the one or more property changes to the one or more chemical species during a time interval; and a process controller configured to fit the continuous stream of data to a mathematical function to predict one or more properties of the one or more chemical species at a future time point and make one or more process decisions based on the prediction of one or more properties at the future time point.

Statement 20: A device according to Statement 19, wherein the time-dependent process is a chemical reaction.

Statement 21: A device according to any one of Statements 19-20, wherein the time-dependent process is a polymerization reaction.

Statement 22: A device according to any one of Statements 19-21, wherein the one or more process decisions comprise any one of terminating of the time-dependent process, recovering the reactor contents, proceeding to a subsequent reaction or processing stage in the same or a different reactor.

Statement 23: A device according to any one of Statements 19-22, wherein the process controller is further configured to direct a change in one or more conditions of the time-dependent process to alter the predicted one or more properties of the chemical species at the future time point.

Statement 24: A device according to Statement 23, wherein the one or more conditions comprise any one of reactor pressure, reactor temperature, reaction stir rate, reaction agitation rate, reactant concentration, reagent concentration, or reagent flow rate.

Statement 25: A device according to any one of Statements 19-24, wherein the one or more property changes comprises changes in concentration of the one or more chemical species.

Statement 26: A device according to any one of Statements 19-25, wherein the one or more property changes comprises changes in molecular weight of the one or more chemical species.

Statement 27: A device according to any one of Statements 19-26, wherein the one or more detectors is configured for measuring any one or more of UV absorption, infra-red absorption, Raman scattering, fluorescence, conductivity, reduced viscosity, dynamic light scattering, static light scattering, Mie scattering, evaporative light scattering, refractive index detection, linear birefringence, circular birefringence, linear dichroism, circular dichroism, infrared detection, NMR, and polarimetry.

Statement 28: A device according to any one of Statements 19-27, wherein one or more of the reactor, the extractor pump, the one or more detectors, and the process controller are incorporated in an automatic continuous online monitoring of polymerization (ACOMP) system.

Statement 29: A device according to any one of Statements 19-27, further comprising a means of diluting and/or conditioning the one or more extracted contents.

Statement 30: A device according to Statement 29, wherein one or more of the reactor, the extractor pump, the one or more detectors, the process controller and the means of diluting and/or conditioning are incorporated in an automatic continuous online monitoring of polymerization (ACOMP) system.

Statement 31: A device according to any one of Statements 19-30, wherein the reactor is any one of a batch reactor, a semi-batch reactor, and a continuous reactor.

The foregoing descriptions of specific compositions and methods of the present disclosure have been presented for purposes of illustration and description. They are not intended to be exhaustive or to limit the disclosure to the precise compositions and methods disclosed and obviously many modifications and variations are possible in light of the above teaching. The examples were chosen and described in order to best explain the principles of the disclosure and its practical application, to thereby enable others skilled in the art to best utilize the disclosure with various modifications as are suited to the particular use contemplated. It is intended that the scope of the disclosure be defined by the claims appended hereto and their equivalents.

What is claimed is:

1. A method comprising:
   introducing, in a reactor, one or more chemical species to be monitored during a time-dependent process;
   detecting, using one or more detectors, one or more property changes to the one or more chemical species over a time interval;
   receiving, from the one or more detectors, a continuous stream of data related to the one or more property changes to the one or more chemical species during the time interval;
   fitting, using a process controller, the continuous stream of data to a mathematical function to predict one or more properties of the one or more chemical species at a future time point; and
   making, by the process controller, one or more process decisions based on the prediction of one or more properties at the future time point.

2. The method of claim 1, wherein the one or more process decisions comprise any one of terminating of the time-dependent process, recovering the reactor contents, proceeding to a subsequent reaction or processing stage in the same or a different reactor.

3. The method of claim 1, further comprising fitting the continuous stream of data to a function to predict a grade changeover between a first polymerization reaction product and a second polymerization reaction product of the polymerization reaction, wherein the time-dependent process is a polymerization reaction, and wherein
   one of the one or more detectors is a viscometer; and
   the predicted grade changeover is derived from reduced viscosity measurements detected by the viscometer during the time interval.

4. The method of claim 3, wherein the predicted grade changeover is derived from reduced viscosity measurements and correlated to offline Mooney Viscosity measurements.

5. The method of claim 4, wherein the one or more property changes comprises changes in viscosity of a polymer product formed during the polymerization reaction.

6. The method of claim 4, wherein the one or more property changes comprises changes in molecular weight of a polymer product formed during the polymerization reaction.

7. The method of claim 1, further comprising:
   changing, using the process controller, one or more conditions of the time-dependent process to alter the predicted one or more properties of the chemical species at the future time point, wherein the one or more conditions comprise any one of reactor pressure, reactor temperature, reaction stir rate, reaction agitation rate, reactant concentration, reagent concentration, or reagent flow rate into the reactor.

8. The method of claim 1, wherein the one or more property changes comprise changes in any one of concentration, molecular weight, polydispersity, reduced viscosity, intrinsic viscosity, and chemical composition of the one or more chemical species.

9. The method of claim 8, further comprising:
   predicting a time period required for a residual chemical species concentration to reach one or more specified levels; and
   changing, using the process controller, one or more conditions of the time-dependent process to alter the predicted residual chemical species concentration at a future time point.

10. The method of claim 1, wherein the method is performed using an Automatic Continuous Online Monitoring of Polymerization reactions (ACOMP) system, the ACOMP system comprising the reactor, the one or more detectors and the process controller.

11. A device comprising:
    a reactor for containing one or more chemical species of a time-dependent process;
    an extraction pump for automatically and continuously extracting an amount of the one or more chemical species from the reactor;
    one or more detectors for measuring property changes of the one or more extracted chemical species and generating a continuous stream of data related to the one or more property changes to the one or more chemical species during a time interval; and
    a process controller configured to fit the continuous stream of data to a mathematical function to predict one or more properties of the one or more chemical species at a future time point and make one or more process decisions based on the prediction of one or more properties at the future time point.

12. The device of claim 11, wherein the one or more process decisions comprise any one of terminating of the time-dependent process, recovering the reactor contents, proceeding to a subsequent reaction or processing stage in the same or a different reactor.

13. The device of claim 11, wherein the process controller is further configured to direct a change in one or more conditions of the time-dependent process to alter the predicted one or more properties of the chemical species at the future time point.

14. The device of claim 13, wherein the one or more conditions comprise any one of reactor pressure, reactor temperature, reaction stir rate, reaction agitation rate, reactant concentration, reagent concentration, or reagent flow rate.

15. The device of claim 11, wherein the one or more property changes comprises changes in concentration of the one or more chemical species.

16. The device of claim 11, wherein the one or more property changes comprises changes in molecular weight of the one or more chemical species.

17. The device of claim 11, wherein the one or more detectors is configured for measuring any one or more of UV absorption, infra-red absorption, Raman scattering, fluorescence, conductivity, reduced viscosity, dynamic light scattering, static light scattering, Mie scattering, evaporative light scattering, refractive index detection, linear birefringence, circular birefringence, linear dichroism, circular dichroism, infrared detection, NMR, and polarimetry.

18. The device of claim 11, wherein one or more of the reactor, the extraction pump, the one or more detectors, and the process controller are incorporated in an automatic continuous online monitoring of polymerization (ACOMP) system.

19. The device of claim 11, further comprising a means of diluting and/or conditioning the one or more extracted contents.

20. The device of claim 19, wherein one or more of the reactor, the extraction pump, the one or more detectors, the process controller and the means of diluting and/or conditioning are incorporated in an automatic continuous online monitoring of polymerization (ACOMP) system.

* * * * *